United States Patent
Al-Eid et al.

(10) Patent No.: US 11,278,873 B2
(45) Date of Patent: Mar. 22, 2022

(54) METHOD OF PRODUCING AN AROMATIZATION CATALYST

(71) Applicant: Saudi Arabian Oil Company, Dhahran (SA)

(72) Inventors: Manal Al-Eid, Dhahran (SA); Lianhui Ding, Dhahran (SA); Essa Alnaimi, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 16/930,462

(22) Filed: Jul. 16, 2020

(65) Prior Publication Data

US 2022/0016609 A1 Jan. 20, 2022

(51) Int. Cl.

| B01J 29/06 | (2006.01) |
|---|---|
| B01J 29/40 | (2006.01) |
| B01J 37/02 | (2006.01) |
| B01J 37/00 | (2006.01) |
| B01J 37/08 | (2006.01) |
| B01J 35/00 | (2006.01) |
| B01J 35/10 | (2006.01) |
| B01J 37/10 | (2006.01) |
| B82Y 30/00 | (2011.01) |

(52) U.S. Cl.
CPC ............ B01J 29/405 (2013.01); B01J 35/006 (2013.01); B01J 35/1019 (2013.01); B01J 35/1023 (2013.01); B01J 35/1038 (2013.01); B01J 35/1042 (2013.01); B01J 35/1061 (2013.01); B01J 35/1066 (2013.01); B01J 37/0009 (2013.01); B01J 37/0207 (2013.01); B01J 37/0236 (2013.01); B01J 37/086 (2013.01); B01J 37/10 (2013.01); B01J 37/105 (2013.01); B01J 2229/20 (2013.01); B01J 2229/42 (2013.01); B82Y 30/00 (2013.01)

(58) Field of Classification Search
CPC .. B01J 29/405; B01J 2229/20; B01J 2229/42; B01J 2229/36; B01J 23/28; B01J 23/30; B01J 21/04; B01J 21/08; B01J 6/001; B01J 35/006; B01J 35/1019; B01J 35/1023; B01J 35/1038; B01J 35/1042; B01J 35/1061; B01J 35/1066; B01J 35/023; B01J 37/0009; B01J 37/0207; B01J 37/0236; B01J 37/086; B01J 37/10; B01J 37/105; B01J 37/04; B82Y 30/00
USPC ............................ 502/60, 61, 63, 64, 69, 71
See application file for complete search history.

(56) References Cited

U.S. PATENT DOCUMENTS

| 5,026,937 | A | 6/1991 | Bricker |
| 6,133,186 | A | 10/2000 | Gosselink et al. |
| 6,762,143 | B2 | 7/2004 | Shan et al. |
| 7,550,405 | B2 | 6/2009 | Shan et al. |
| 2009/0272674 | A1 | 11/2009 | Zheng et al. |
| 2010/0179361 | A1 | 7/2010 | Goergen et al. |
| 2017/0144138 | A1 | 5/2017 | Arvind et al. |
| 2017/0291167 | A1* | 10/2017 | Ding ............ B01J 29/061 |
| 2017/0369397 | A1* | 12/2017 | Al-Herz ........... B01J 29/80 |
| 2018/0333708 | A1* | 11/2018 | Ding ............ B01J 29/7007 |

FOREIGN PATENT DOCUMENTS

| KR | 101695105 B1 | 1/2017 |
| WO | 2017180458 A1 | 10/2017 |
| WO | WO 2017/180458 | * 10/2017 |
| WO | WO 2018/212984 | * 11/2018 |
| WO | 2020106628 A1 | 5/2020 |

OTHER PUBLICATIONS

Yingxia Li. et al., "Transalkylation of Multi-secbutylbenzenes over hierarchical Beta Zeolite", Chinese Journal of Chemical Engineering, 22, 2014, pp. 898-902.*
Matsukata et al., "Crystallization behaviour of zeolite beta during steam-assisted crystallization of dry gel", Microporous and Mesoporous Materials, 56, 2002, pp. 1-10.*
Mohammadparast et al., "The synthesis of nano-sized ZSM-5 zeolite by dry gel conversion method and investigating the effects of experimental parameters by Taguchi experimental design", Journal of Experimental Nanoscience, Vo. 13, No. 1, 2018, pp. 160-173.*
Rao et al., "Dry-gel conversion technique for synthesis of zeolite BEA", Chem. Commun., 1996, pp. 1441-1442.*
Van Grieken et al. "Anomalous crystallization mechanism in the synthesis of nanocrystalline zeolite Beta in the absence of alkali metal cations", Studies in Surface Science and Catalysis, vol. 105, 1997, pp. 341-348.*
International Search Report and Written Opinion dated Apr. 19, 2021 pertaining to International application No. PCT/US2020/052696 filed Sep. 25, 2020, 16 pgs.
Jia, Y. et al. "Hierarchical ZSM-5 zeolite synthesized via dry gel conversion-steam assisted crystallization process and its application in aromatization of methanol", Powder Technology, vol. 328, Apr. 1, 2018, pp. 415-429.
Ding, L. et al. "LCO hydrotreating with Mo—Ni and W—Ni supported on nano- and micro-sized zeolite beta", Applied Catalysis A: General, Elsevier, Amsterdam, NL, vol. 353, No. 1, Jan. 31, 2009, pp. 17-23.

(Continued)

Primary Examiner — Elizabeth D Wood
(74) Attorney, Agent, or Firm — Dinsmore + Shohl LLP

(57) ABSTRACT

According to the subject matter of the present disclosure, a method of producing an aromatization catalyst may comprise producing a plurality of uncalcined ZSM-5 nanoparticles via a dry-gel method, directly mixing the plurality of uncalcined ZSM-5 nanoparticles with large pore alumina and a binder to form a ZSM-5/alumina mixture, and calcining the ZSM-5/alumina mixture to form the aromatization catalyst. The plurality of uncalcined ZSM-5 nanoparticles may have an average diameter of less than 80 nm.

17 Claims, 1 Drawing Sheet

(56) References Cited

OTHER PUBLICATIONS

Yue, M. B. et al. Dry-gel synthesis of shaped binderless zeolites composed of nanosized ZSM-5, Solid State Sciences, vol. 20, Jun. 1, 2013, pp. 1-7.

Su, X. F. et al "Conversion of Methanol to Aromatic-Rich Gasoline over High-Efficiency Bifunctional Catalysts: Green Synthesis of GaZSM-5 Zeolites via Dry-Gel Conversion Strategy", Russian Journal of Applied Chemistry, Pleiades Publishing, Moscow, vol. 93, No. 1, Jan. 1, 2020, pp. 127-136.

Ding et al., "Nanocrystalline zeolite beta: The effect of template agent on crystal size", Materials Research Bulletin, vol. 42, pp. 584-590, 2007.

Kecht et al., "Nanosized Zeolites Templated by Metal—Amine Complexes", Chemistry of Materials, vol. 19, No. 6, pp. 1203-1205, Mar. 20, 2007.

Lechert, "The mechanism of faujasite growth studied by crystallization kinetics", Zeolites, vol. 17, pp. 473-482, 1996.

Mintova et al., Variation of the Si/Al ratio in nanosized zeolite Beta crystals, Microporous and Mesoporous Matereials, vol. 90, pp. 237-245, 2006.

Naik et al.., "Synthesis of Zeolitic Mesoporous Materials by Dry Gel Conversio under Controlled Humidity", J. Phys. Chem B, vol. 107, pp. 7006-7014, 2003.

Sakthievel et al., "Nanosized B-zeolites with tunable particle sizes: Synthesis by the dry gel conversion (DGC) method in the presence of surfactants, chractereiation and catalytic propeties", Microporous and Mesoporous Materials, vol. 119, pp. 332-330, 2009.

Tsapatsis et al., "Characterization of Zeolite L. Nanoclusters" Chem. Magter, vol. 7, pp. 1734-1741, 1995.

Xia et al., "Crystallizatio kinetics of nanosized TiB zeolites with high oxidation activity by a dry-gel conversion technique", Materials Chemistry and Physics, vol. 89, pp. 89-98, 2005.

U.S. Notice of Allowance dated Aug. 5, 2021 pertaining to U.S. Appl. No. 16/921,124, filed Jul. 6, 2020, 12 pages.

Office Action dated Jun. 3, 2021 pertaining to U.S. Appl. No. 16/921,124, filed Jul. 6, 2020, 24 pages.

Camblor, M.A. et al, "Synthesis of nanocrystalline zeolite Beta in the absence of alkali metal cations", Studies in Surface Science and Catalysis, vol. 105, 1997, pp. 341-348.

International Search Report and Written Opinion dated Oct. 22, 2021 pertaining to International application No. PCT/US2021/040500 filed Jul. 6, 2021.

* cited by examiner

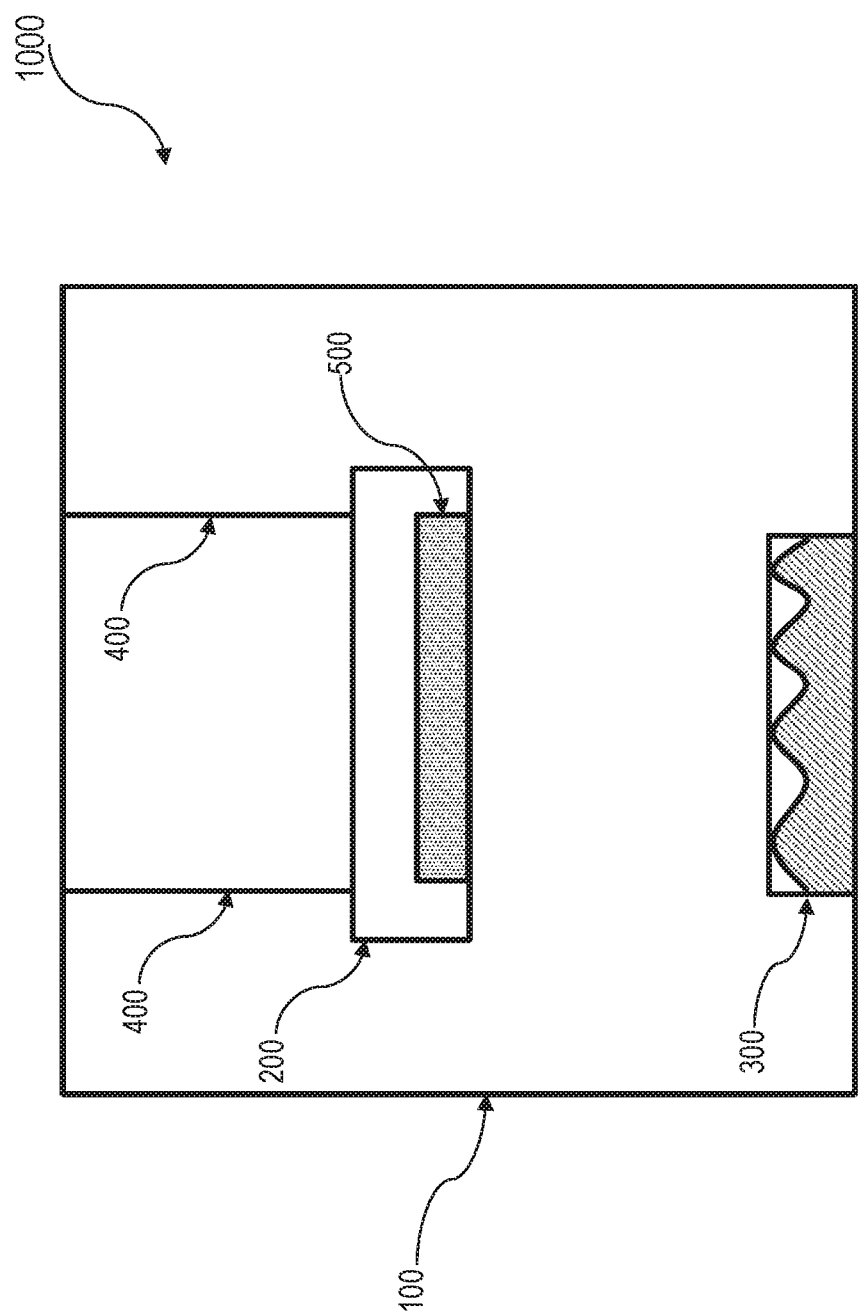

METHOD OF PRODUCING AN AROMATIZATION CATALYST

TECHNICAL FIELD

The present disclosure relates to methods of making aromatization catalysts, and more specifically, to methods of making aromatization catalysts which comprise ZSM-5.

BACKGROUND

Catalytic reforming is used to produce benzene, toluene, xylene, alkenes, high octane gasoline, and hydrogen from naphtha. During the naphtha reforming process, low-octane straight chain alkanes (paraffins), with 6 to 10 carbon atoms, are reformed into molecules having branched alkanes (isoparaffins) and cyclic naphthenes, which are then partially dehydrogenated to produce high-octane aromatic hydrocarbons such as benzene, toluene and xylenes (BTX) in the reformate.

Current light naphtha ($C_5$ and $C_6$) aromatization and catalytic reforming technologies focus on conversion of naphthenes and isoparaffins in naphtha feedstock to BTX products. ZSM-5 zeolite has been used in light naphtha aromatization. However, due to the simple microporous structure and long diffusion pathways of ZSM-5, ZSM-5 suffers from rapid deactivation of its catalytic sites and insufficient diffusion of the target molecules to the ZSM-5 active sites.

One solution to the diffusion length and pore size problems is to reduce zeolite particle size, thereby increasing external surface area and decreasing diffusion lengths. However, while reduced particle size should lead to greatly improved catalytic activity, agglomeration of the nano-sized zeolite particles of the catalyst may occur and thereby prevent this improved catalytic activity.

SUMMARY

Accordingly, there is a continual need for aromatization catalysts and methods of making those aromatization catalysts, which can eliminate the agglomeration of zeolite particles and thereby improve the catalytic activity of the aromatization catalysts. Embodiments of the present disclosure meet this need by producing aromatization catalysts comprising ZSM-5 synthesized by a dry-gel method. Embodiments further meet this need by postponing the calcining step until after the ZSM-5 is mixed with other catalyst components.

According to one embodiment of the present disclosure, a method of producing an aromatization catalyst may comprise producing a plurality of uncalcined ZSM-5 nanoparticles via a dry-gel method, directly mixing the plurality of uncalcined ZSM-5 nanoparticles with large pore alumina and a binder to form a ZSM-5/alumina mixture, and calcining the ZSM-5/alumina mixture to form the aromatization catalyst.

In accordance with one embodiment of the present disclosure, producing a plurality of uncalcined ZSM-5 nanoparticles via a dry-gel method may comprise combining an alumina source, a structure directing agent, and a silica source to form a slurry; drying the slurry to form a dry-gel; and autoclaving the dry-gel in a humidified autoclave to form the plurality of uncalcined ZSM-5 nanoparticles.

Although the concepts of the present disclosure are described herein with primary reference to aromatization catalysts, it is contemplated that the concepts will enjoy applicability to any catalytic system.

BRIEF DESCRIPTION OF THE DRAWING

The following detailed description of specific embodiments of the present disclosure can be best understood when read in conjunction with the following drawing:

FIG. 1 shows the layout of a humidified autoclave.

ABBREVIATIONS

ASTM=American Society for Testing and Materials.
BET surface area=Brunauer-Emmett-Teller surface area.
° C.=degrees Celsius.
g/l=grams per liter.
g=grams.
hr.=hour.
min.=minute.
$m^2$/g=meters squared per gram.
$MoO_3$=molybdenum trioxide.
NiO=nickel oxide.
nm=nanometers.
OSDAs=organic structure-directing agents.
PSIG=Pounds per square inch gauge.
rpm=revolutions per minute.
TEAOH=tetraethylammonium hydroxide.
TMAOH=tetramethylammonium hydroxide.
TEOS=tetraethyl orthosilicate.
wt. %=weight percent.

DETAILED DESCRIPTION

In naphtha aromatization, smaller catalytic particles, such as ZSM-5 nanoparticles, are theoretically desirable as smaller particles have a higher surface area to mass ratio. However, a practical limit on the size of nanoparticles is imposed by the problem of agglomeration. When small particles are placed near one another, the attractive forces can overwhelm the repulsive forces, and multiple particles can combine to form a single larger particle. Thus, negating the effect of the smaller particle size. As ZSM-5 nanoparticles are used in aromatization catalysts, it is desirable to prevent agglomeration in the production of ZSM-5 nanoparticles.

In the formation of ZSM-5 nanoparticles according to conventional methods, this agglomeration is believed to occur primarily during the centrifuging and calcining steps. Without being limited by theory, it is believed that certain modifications will lead to decreased nanoparticle agglomeration. Specifically, those modifications are the elimination of the centrifuging step and postponing the calcining step until after the ZSM-5 nanoparticles are mixed with the large pore alumina and binder.

Embodiments of the present disclosure are directed to improved methods that decrease agglomeration. For example, a method of producing an aromatization catalyst may include producing a plurality of uncalcined ZSM-5 nanoparticles via a dry-gel method. The plurality of uncalcined ZSM-5 nanoparticles may be directly mixed with large pore alumina and binder to form a ZSM-5/alumina mixture. The ZSM-5/alumina mixture may then be calcined to form the aromatization catalyst.

The plurality of uncalcined ZSM-5 nanoparticles may be produced via a dry-gel method. In one or more embodiments, the dry-gel method may comprise combining an alumina source, a structure directing agent, and a silica source to form a slurry; drying the slurry to form a dry-gel; and autoclaving the dry-gel in a humidified autoclave to form the plurality of uncalcined ZSM-5 nanoparticles.

Producing the plurality of uncalcined ZSM-5 nanoparticles may comprise drying the slurry to form a dry-gel. A dry-gel may include a slurry where the water content of the slurry is substantially equilibrated with the surrounding atmosphere. The slurry may be dried in an oven or under vacuum.

The water content of the dry-gel may be less than 25 wt. %. For example, the water content of the dry-gel may be less than 20 wt. %, less than 15 wt. %, less than 10 wt. %, less than 5 wt. %, or even less than 1 wt. %, or any subset thereof.

The slurry may be dried at a specified temperature and pressure. For example, the slurry may be dried at less than or equal to atmospheric pressure and a temperature of from 80° C. to 140° C., from 90° C. to 130° C., or from 100° C. to 120° C. According to some embodiments, the slurry may be dried at less than or equal to −4 PSIG and a temperature of from 80° C. to 140° C., from 90° C. to 130° C., or from 100° C. to 120° C. According to further embodiments, the slurry may be dried at less than or equal to −8 PSIG and a temperature of from 80° C. to 140° C., from 90° C. to 130° C., or from 100° C. to 120° C., or any subset thereof.

The slurry may be dried for a specified period of time. For example, the slurry may be dried for from 1 hr. to 7 days, from 6 hr. to 7 days, from 12 hr. to 7 days, from 24 hr. to 7 days, from 1 hr. to 6 days, from 1 hr. to 5 days, from 1 hr. to 4 days, from 1 hr. to 3 days, from 4 hr. to 3 days, from 8 hr. to 2 days, or any subset thereof.

Drying the slurry may take place in the absence of agitation. For example, the slurry may be dried without any mixing, spinning, stirring, shaking, or other form of agitation.

The dry-gel may be autoclaved in a humidified autoclave to form a plurality of uncalcined ZSM-5 nanoparticles. An autoclave may include any device or combination of devices suitable to maintain a specified temperature and humidity. Referring to FIG. 1, the humidified autoclave 1000 may be a sealed chamber 100 with a sample holder 200, wherein the sealed chamber may be placed inside an oven. Specifically as shown, the humidified autoclave 1000 may comprise a sealed chamber 100. Inside the sealed chamber 100, there may be a sample holder 200. Optionally, there may be a water holder 300. The sample holder 200 may be connected to the exterior of the sealed chamber 100 by a plurality of supports 400. The dry-gel 500 may be placed in the sample holder 200.

A relative humidity in the humidified autoclave may be from 1% to 100%. For example, the relative humidity may be from 1% to 99%, from 1% to 75%, from 1% to 50%, from 25% to 100%, from 25% to 75%, from 25% to 50%, from 50% to 100%, from 50% to 75%, from 75% to 100%, from 75% to 90%, from 90% to 10%, or any subset thereof. According to some embodiments, the atmosphere within the humidified autoclave may comprise saturated steam.

According to some embodiments, the dry-gel may not be agitated during the autoclaving process. For example, the dry-gel may be autoclaved without any mixing, spinning, shaking, or stirring.

The dry-gel may be autoclaved at 100° C. to 225° C. for 1 day to 10 days For example, the dry-gel may be autoclaved at 100° C. to 200° C., 100° C. to 175° C., 125° C. to 200° C., 125° C. to 175° C., or 150° C. to 225° C.; for 1 day to 8 days, 1 day to 5 days, 1 day to 4 days, 1 day to 3 days, 1 day to 2 days, 2 days to 8 days, 2 days to 6 days, 2 days to 5 days, 2 days to 4 days, 3 days to 8 days, 4 days to 6 days, or any subset thereof.

As stated above, the alumina source, structure directing agent, and silica source may be combined to form a slurry. The slurry may further comprise water or a non-aqueous solvent. According to some embodiments, the structure directing agent itself may serve as the solvent. The combining may take the form of stirring, mixing, shaking, or agitating.

The alumina source may comprise any chemical precursor capable of releasing aluminum ions or particles into the slurry. For example, the alumina source may include sodium aluminate, aluminum chloride, aluminum nitrate, powdered aluminum metal, powdered alumina, or any combination thereof.

Various compositions are contemplated for the structure directing agent. In one or more embodiments, the structure directing agent may comprise one or more of tetrapropylammonium hydroxide (TPAOH), tetraethylammonium hydroxide (TEAOH), or tetramethylammonium hydroxide (TMAOH). The structure directing agent may comprise organic structure-directing agents (OSDAs) such as organic ammonium, inorganic cations such as sodium, or both. According to some embodiments, the structure directing agent may comprise TPAOH.

The silica source may comprise any chemical precursor capable of releasing silica into the slurry. For example, the silica source may include fumed silica, solid silica gel, white carbon, or tetraethyl orthosilicate (TEOS).

According to some embodiments, the dry-gel method may comprise introducing NaOH to the slurry such that the final concentration of NaOH in the slurry is from 0.000001 g/L to 0.1 g/L. For example, the final concentration of NaOH in the slurry may be from 0.000001 g/L to 0.01 g/L, from 0.000001 g/L to 0.001 g/L, from 0.000001 g/L to 0.001 g/L, or even from 0.000001 g/L to 0.000002 g/L. In embodiments where NaOH is present, it may be preferable to have a relatively small amount of NaOH. Without being limited by theory it is believed that the presence of NaOH causes detrimental effects including irregular zeolite crystal formation and large particle sizes. Another disadvantage of the presence of NaOH is that further $NH_4^+$ ion exchange is then required to reduce the quantity of detrimental sodium in the zeolite. Thus the yield is increased and the cost is decreased when minimal or no NaOH is present.

As stated previously, the plurality of uncalcined ZSM-5 nanoparticles produced by the dry-gel method may be directly mixed with large pore alumina and a binder. According to some embodiments, only a portion of the uncalcined ZSM-5 nanoparticles may be directly mixed with the large pore alumina and binder. Alternatively, all of the produced uncalcined ZSM-5 nanoparticles may be directly mixed with the large pore alumina and binder.

The ZSM-5/alumina mixture may comprise a mixture of solids, a mixture of liquids, or a mixture of some solids and some liquids. For example, the mixture may comprise a slurry, a powder mixture, an aqueous solution, a colloid, a gel, a hydrogel, or any other mixture. According to some embodiments, the mixture may include additional solvents, such as water or a non-aqueous solvent. According to other embodiments, the mixture may not include additional solvents.

As used herein, "ZSM-5" may refer to a hydrated alumino-silicate of framework type MFI and of the general chemical formula $Na_nAl_nSi_{96-n}O_{192} \cdot 16H_2O$ (where 0<n<27). The ZSM-5 may be identified by X-ray diffraction (XRD) peaks at 7.9° 2-theta and 24° 2-theta.

As used herein, "directly mixed" may refer to combining the plurality of uncalcined ZSM-5 nanoparticles with the large pore alumina and binder, without any processing steps which may cause agglomeration between autoclaving the dry-gel and combining the plurality of uncalcined ZSM-5 nanoparticles with the large pore alumina and binder. For example, the excluded processing steps may include one or more of calcination, centrifuging, washing, or ion-exchange.

The step of directly mixing may be any mixing step. For example, directly mixing may include mechanical mixing. The mechanical mixing may encompass extrusion, such as extrusion performed in a twin screw extruder. Mechanical mixing may take place in a static mixer, rotary mixer, mortar and pestle, extruder, or a combination of these. Directly mixing may also include other mixing steps such as impregnation. For example, directly mixing may include both extrusion and impregnation. As used herein, impregnation refers to a process wherein a metal precursor is dissolved in a solution, the catalyst support is inserted into the solution, and the metal precursor is drawn into the support by capillary and diffusive forces.

The large pore alumina may have a pore volume of 0.7 ml/g to 1.2 ml/g. For example, the pore volume may be from 0.8 ml/g to 1.1 ml/g, or from 0.9 ml/g to 1.0 ml/g. The large pore alumina may have a pore size of 18 nm to 26 nm. For example, the pore size may be from 20 nm to 24 nm. The pore volume and pore size of the large pore alumina may be calculated according to the Barret-Joyner-Halenda (BJH) method.

The aromatization catalyst may comprise from 0 wt. % to 30 wt. % of the large pore alumina. For example, the aromatization catalyst may comprise from 5 wt. % to 30 wt. %, from 10 wt. % to 30 wt. %, from 20 wt. % to 30 wt. %, from 0 wt. % to 20 wt. %, from 0 wt. % to 10 wt. %, from 10 wt. % to 30 wt. %, from 10 wt. % to 20 wt. %, or any subset thereof, of the large pore alumina.

The aromatization catalyst may comprise from 10 wt. % to 20 wt. % of the binder. For example, the aromatization catalyst may comprise 10 wt. % to 17.5 wt. %, from 12.5 wt. % to 20 wt. %, from 12.5 wt. % to 17.5 wt. %, from 10 wt. % to 15 wt. %, from 15 wt. % to 20 wt. %, or any subset thereof, of the binder.

As used herein, a binder may refer to any substance capable of holding the hydrocracking components together. However, it is known that the choice of binder can have a significant effect on acidity and thus on the suitability of a zeolite based catalyst for its particular catalytic task. According to some embodiments, the binder may comprise one or more of a clay, a mineral, an alumina, or a silica. The clay may comprise kaolin. The alumina may comprise one or more of attapulgite, boehmite, or partially acid peptized alumina. According to some specific embodiments, the binder may comprise a partially acid peptized alumina. The partially acid peptized alumina may comprise small pore alumina with an alumina pore volume of 0.4 ml/g to 0.6 ml/g and a $HNO_3$/alumina molar ratio of 0.2 to 0.3

Centrifugation and calcination are believed to be the most significant causes of agglomeration during the production of ZSM-5 nanoparticles. By eliminating or postponing these processes until after the ZSM-5 nanoparticles are mixed with the large pore alumina and binder, agglomeration can be greatly reduced.

Without being limited by theory, it is believed that the centripetal forces of centrifugation tend to compress the nanoparticles into a smaller space, causing them to come into contact and agglomerate.

The plurality of uncalcined ZSM-5 nanoparticles may have not been subjected to centrifugation before being mixed with the large pore alumina and binder. As used herein, "centrifugation" may refer to spinning in a centrifuge above 3,000 rpm, 5,000 rpm, 8,000 rpm, 10,000 rpm, or even 20,000 rpm, or any subset thereof.

Without being limited by theory, it is believed that calcination may cause agglomeration through a process known as sintering. At elevated temperatures, diffused matter may form bridge-like structures between the surfaces.

The plurality of uncalcined ZSM-5 nanoparticles may also not have been subjected to calcination prior to being mixed with the large pore alumina and binder. As used herein "calcination" may refer to exposure to temperatures above 200° C., above 300° C., above 400° C., or above 500° C.; for more than 30 minutes, more than 45 minutes, more than 60 minutes, more than 90 minutes, more than 180 minutes, more than 5 hours, more than 8 hours, more than 12 hours, more than 24 hours, more than 48 hours, or more than 5 days, or any subset thereof.

It should be understood that the plurality of uncalcined ZSM-5 nanoparticles may not have been subjected to either centrifugation or calcination during the time between formation and mixing with the large pore alumina and binder. For example, the plurality of uncalcined ZSM-5 nanoparticles may not have been centrifuged or calcined after autoclaving the dry-gel and before mixing the dry-gel with the large pore alumina and binder. The plurality of uncalcined ZSM-5 nanoparticles may not have been centrifuged or calcined after the combining of the alumina source, the silica source, and the structure directing agent and before mixing with the large pore alumina and binder.

While the process of calcination may cause undesirable agglomeration before the uncalcined ZSM-5 nanoparticles have been mixed with the large pore alumina and binder, it is useful in the formation of a catalyst. The calcined catalyst is believed to better withstand the rigors of a chemical reactor.

The catalyst may be dried before calcination. Drying the catalyst may comprise exposing the catalyst to temperatures between 25° C. and 350° C. For example, the temperature may be between 50° C. and 325° C., 75° C. and 300° C., 100° C. and 275° C., 150° C. and 225° C., or any subset thereof. Drying the catalyst may comprise exposing the catalyst to the elevated temperatures for from 2 hr. to 24 hr. For example, the catalyst may be exposed to the elevated temperature for from 6 hr. to 20 hr., or 12 hr. to 14 hr., or any subset thereof. Without being limited by theory, it is believed that drying may be necessary to prevent the buildup of steam from damaging the catalyst during calcination.

The ZSM-5/alumina mixture may be calcined to form the aromatization catalyst. It should be understood that the ZSM-5/alumina mixture which may be calcined comprises the uncalcined ZSM-5 nanoparticles, the large pore alumina, and the binder.

The ZSM-5/large pore alumina mixture may be calcined at 400° C. to 700° C., for 1 hour to 10 hours. For example, the ZSM-5/large pore alumina mixture may be calcined at 400° C. to 600° C., 400° C. to 500° C., 500° C. to 700° C., 600° C. to 700° C., or 500° C. to 600° C.; for 1 hour to 9 hours, 1 hour to 8 hours, 1 hour to 6 hours, 2 hours to 10 hours, 2 hours to 9 hours, 2 hours to 7 hours, 4 hours to 10 hours, 4 hours, to 8 hours, or 4 hours to 6 hours, or any subset thereof.

The plurality of uncalcined ZSM-5 nanoparticles may have an average diameter of less than 80 nm. For example, the plurality of uncalcined ZSM-5 nanoparticles may have an average diameter of less than 70 nm, less than 60 nm, less than 50 nm, less than 40 nm, or less than 30 nm, or any subset thereof. It should be understood that the average diameter is the mean diameter and is to be calculated using all the uncalcined ZSM-5 nanoparticles introduced into the mixture. The diameter of the uncalcined ZSM-5 nanoparticles may be determined by TEM.

The plurality of uncalcined ZSM-5 nanoparticles may have an average diameter of from 30 nm to 80 nm. For example, the average diameter may be from 20 nm to 40 nm, from 20 nm to 30 nm, from 30 nm to 50 nm, from 40 nm to 50 nm, or any subset thereof.

At least 90% of the individual uncalcined ZSM-5 nanoparticles may have diameters of from 20 nm to 50 nm. For example, at least 90% of the ZSM-5 nanoparticles may have diameters from 20 nm to 40 nm, from 20 nm to 30 nm, from 30 nm to 50 nm, or from 40 nm to 50 nm, or any subset thereof.

A silica/alumina ratio of the uncalcined ZSM-5 nanoparticles may be from 20 to 100. For example, the silica/alumina molar ratio may be from 20 to 90, 20 to 75, 20 to 50, 20 to 40, 30 to 100, 30 to 75, 30 to 50, 30 to 40, 35 to 100, 35 to 75, 35 to 50, 35 to 40, or any subset thereof.

An average pore size of the uncalcined ZSM-5 nanoparticles may be from 35 nm to 55 nm. For example, the average pore size of the uncalcined ZSM-5 nanoparticles may be from 40 nm to 50 nm, from 35 nm to 45 nm, from 45 nm to 55 nm, or any subset thereof.

The surface area of both the calcined and uncalcined ZSM-5 nanoparticles may be measured using BET analysis and calculated with the multipoint BET equation. Pore volume of both the calcined and uncalcined ZSM-5 nanoparticles may be calculated from the maximum adsorption amount of nitrogen. The pore size distribution of both the calcined and uncalcined ZSM-5 nanoparticles may be determined based on the Barrett-Joyner-Halenda (BJH) method and the desorption branch of the isotherm. The average pore sizes of both the calcined and uncalcined ZSM-5 nanoparticles may be calculated by the equation $Ps=4V/S$, where $Ps$=pore size, $V$=pore volume, and $S$=surface area.

A BET surface area of the uncalcined ZSM-5 nanoparticles may be from 300 $m^2/g$ to 600 $m^2/g$. For example, the BET surface area may be from 200 $m^2/g$ to 600 $m^2/g$, from 300 $m^2/g$ to 500 $m^2/g$, from 400 $m^2/g$ to 500 $m^2/g$, or from 500 $m^2/g$ to 600 $m^2/g$, or any subset thereof.

The pore volume of the uncalcined ZSM-5 nanoparticles may be from 0.3 ml/g to 0.45 ml/g. For example, the pore volume of the uncalcined ZSM-5 nanoparticles may be from 0.3 ml/g to 0.4 ml/g, from 0.4 ml/g to 0.45 ml/g, from 0.35 ml/g to 0.45 ml/g, or from 0.35 ml/g to 0.40 ml/g, or any subset thereof.

A crystallinity of the uncalcined ZSM-5 nanoparticles may be from 80% to 120%, relative to CBV-5524. For example, the relative crystallinity of the uncalcined ZSM-5 nanoparticles may be from 90% to 110%, or from 95% to 100%, or any subset thereof. CBV-5524 may be commercially available from Zeolyst International.

The crystallinity and phase purity of solid products may be measured by powder X-ray diffraction (XRD) using a diffractometer, such as a Rigaku Ultima IV multi-purpose diffractometer with a copper X-ray tube. The scanning range may be set between 2° to 50° in 2θ Bragg-angles with a step size of 0.04° and a total counting time of 1° per minute. The crystallinity percentage may be calculated by PANalytical High Score Plus software through the comparison of the area under the most intense diffraction peaks to that of patterns of a reference zeolite ZSM 5. The reference zeolite ZSM-5 may be a commercially available zeolite, such as CBV-5524.

The aromatization catalyst may include a plurality of ZSM-5 nanoparticles incorporated within the calcined ZSM-5/alumina mixture. The aromatization catalyst may comprise from 50 wt. % to 90 wt. % of the ZSM-5 nanoparticles. For example, the aromatization catalyst may comprise from 50 wt. % to 70 wt. %, from 70 wt. % to 90 wt. %, from 60 wt. % to 90 wt. %, from 60 wt. % to 80 wt. %, from 50 wt. % to 80 wt. %, or any subset thereof, of the ZSM-5 nanoparticles.

The plurality of ZSM-5 nanoparticles incorporated within the calcined aromatization catalyst may have an average diameter of less than 80 nm. For example, the plurality of ZSM-5 nanoparticles incorporated within the calcined aromatization catalyst may have an average diameter of less than 70 nm, less than 60 nm, less than 50 nm, less than 40 nm, or less than 30 nm, or any subset thereof. It should be understood that the average diameter is the mean diameter and is to be calculated using all the ZSM-5 nanoparticles in the mixture.

Particle sizes may be measured by transmission electron microscopy (TEM). The TEM may be operated at about 200 kV. The average particle sizes may be obtained by measuring all the particles in 5 to 8 TEM images and taking the mean.

The plurality of ZSM-5 nanoparticles incorporated within the calcined aromatization catalyst may have an average diameter from 30 nm to 80 nm. For example, the average diameter may be from 20 nm to 40 nm, from 20 nm to 30 nm, from 30 nm to 50 nm, from 40 nm to 50 nm, or any subset thereof.

At least 90% of the individual ZSM-5 nanoparticles incorporated within the calcined aromatization catalyst may have diameters from 20 nm to 50 nm. For example, at least 90% of the individual ZSM-5 nanoparticles incorporated within the calcined aromatization catalyst may have diameters from 20 nm to 40 nm, from 20 nm to 30 nm, from 30 nm to 50 nm, or from 40 nm to 50 nm, or any subset thereof. For example, at least 95% of the individual ZSM-5 nanoparticles incorporated within the calcined aromatization catalyst may have diameters from 20 nm to 40 nm, from 20 nm to 30 nm, from 30 nm to 50 nm, or from 40 nm to 50 nm, or any subset thereof. For example, at least 99% of the individual ZSM-5 nanoparticles incorporated within the calcined aromatization catalyst may have diameters from 20 nm to 40 nm, from 20 nm to 30 nm, from 30 nm to 50 nm, or from 40 nm to 50 nm, or any subset thereof.

A silica/alumina molar ratio of the plurality of ZSM-5 nanoparticles incorporated within the calcined aromatization catalyst may be from 20 to 100. For example, the silica/alumina molar ratio may be from 20 to 90, 20 to 75, 20 to 50, 20 to 40, 30 to 100, 30 to 75, 30 to 50, 30 to 40, 35 to 40, or any subset thereof.

An average pore size of the plurality of ZSM-5 nanoparticles incorporated within the calcined aromatization catalyst may be from 35 nm to 55 nm. For example, the average pore size of the plurality of ZSM-5 nanoparticles incorporated within the calcined aromatization catalyst may be from 40 nm to 50 nm, from 35 nm to 45 nm, from 45 nm to 55 nm, or any subset thereof. The average pore size may be determined using a gas absorption analyzer, such as the Quantachrome Autosorb iQ.

A BET surface area of the plurality of ZSM-5 nanoparticles incorporated within the calcined aromatization catalyst may be from 300 $m^2/g$ to 600 $m^2/g$. For example, the BET surface area may be from 200 m²/g to 600 m²/g, from 300 m²/g to 500 m²/g, from 400 m²/g to 500 m²/g, or from 500 m²/g to 600 m²/g, or any subset thereof.

The pore volume of the plurality of ZSM-5 nanoparticles incorporated within the calcined aromatization catalyst may be from 0.3 ml/g to 0.45 ml/g. For example, the pore volume of the plurality of ZSM-5 nanoparticles incorporated within the calcined aromatization catalyst may be from 0.3 ml/g to 0.4 ml/g, from 0.4 ml/g to 0.45 ml/g, from 0.35 ml/g to 0.45 ml/g, or from 0.35 ml/g to 0.40 ml/g, or any subset thereof.

A crystallinity of the plurality of ZSM-5 nanoparticles incorporated within the calcined aromatization catalyst may be from 80% to 120%, relative to CBV-5524. For example, the relative crystallinity of the plurality of ZSM-5 nanoparticles incorporated within the calcined aromatization catalyst may be from 90% to 110%, or from 95% to 100%. The crystallinity of the plurality of ZSM-5 nanoparticles incorporated within the calcined aromatization catalyst may be measured by x-ray diffraction (XRD).

The aromatization catalyst may further comprise a catalytic metal. The catalytic metal may be any metal capable of catalyzing an aromatization reaction. For example, the catalytic metal may comprise one or more of W, Al, Ni, Mo, Cr, Mn, Fe, Co, V, Cu, Zn, Ga, Ge, Sn, Cd, Ag, Pd, Pt, Rh, Ru, Nb, or Zr. It should be understood that the catalytic metal may be present in metallic or in oxide form. According to specific embodiments, the catalytic metal may comprise gallium, such as gallium in the form $Ga_2O_3$.

The aromatization catalyst may comprise from 0.2 wt. % to 6 wt. % of the catalytic metal. For example, the aromatization catalyst may comprise from 0.2 wt. % to 4 wt. %, from 0.2 wt. % to 2 wt. %, from 0.2 wt. % to 1 wt. %, from 1 wt. % to 6 wt. %, from 1 wt. % to 3 wt. %, or any subset thereof, of the catalytic metal.

The previously discussed catalytic metal may be introduced to the aromatization catalyst by impregnation after the ZSM-5/alumina mixture is calcined to form an impregnated aromatization catalyst. The aromatization catalyst may be impregnated with the catalytic metal by inserting the calcined aromatization catalyst into an impregnation solution. The impregnation solution may comprise metal precursor compounds which disassociate in the solution to form metals or metal ions. For example, an impregnation solution may comprise gallium nitrate.

According to some embodiments, the aromatization catalyst may be impregnated with gallium atoms to from a Ga-ZSM-5 catalyst. The aromatization catalyst may comprise from 0 wt. % to 10 wt. % of gallium atoms. For example, the aromatization catalyst may comprise from 0 wt. % to 5 wt. %, from 0 wt. % to 4 wt. %, from 1 wt. % to 10 wt. %, from 1 wt. % to 8 wt. %, from 1 wt. % to 5 wt. %, from 2 wt. % to 10 wt. %, from 2 wt. % to 5 wt. %, or from 3 wt. % to 5 wt. %, or any subset thereof, of gallium atoms. After impregnation, the impregnated aromatization catalyst may be dried.

After impregnation, the impregnated aromatization catalyst (also referred to herein as "GA-ZSM-5") catalyst may be further calcined. Without being limited by theory, calcination may be used to drive off remaining volatile compounds such as ammonium, nitric acid, and water. The impregnated aromatization catalyst may be calcined at 400° C. to 700° C. for 1 hour to 10 hours. For example, the impregnated aromatization catalyst may be calcined at 400° C. to 600° C., 400° C. to 500° C., 500° C. to 700° C., 600° C. to 700° C., or 500° C. to 600° C.; for 1 hour to 9 hours, 1 hour to 8 hours, 1 hour to 6 hours, 2 hours to 10 hours, 2 hours to 9 hours, 2 hours to 7 hours, 4 hours to 10 hours, 4 hours, to 8 hours, or 4 hours to 6 hours, or any subset thereof.

EXAMPLES

Catalysts were prepared according to a conventional method and according to the present method. Both catalysts had a composition of 4 wt. % $Ga_2O_3$, 10 wt. % large pore alumina, 20 wt. % partially acid peptized alumina binder, and 66 wt. % of the ZSM-5 nanoparticles characterized in table 1.

Comparative Example 1

1.11 g of aluminum sulfate, 8.1 g of water and 18.1 g of 40 wt. % TPAOH were mixed and stirred at 0° C. Then, 20.83 g of TEOS was added to the mixture and it was stirred at room temperature for 48 hours. The resulting hydrogel was then autoclaved at 170° C. for 5 days. Solid products were then washed and separated in a high-speed centrifuge three times, until the pH was 9. The solid product was then dried in an oven at 110° C. overnight and calcined at 550° C. for 7 hours. The resulting product is characterized in Table 1.

The calcined product was then mixed with appropriate amounts of large pore alumina and partially acid peptized alumina binder to form a mixture. The mixture was extruded into 1.8 mm cylinders, to form a shaped catalyst. The shaped catalyst was dried at 110° C. overnight and then calcined at 500° C. for 4 hours. The calcined catalyst was impregnated with $Ga(NO_3)_3$ solution, then dried and calcined again at 550° C. for 4 hours.

Inventive Example 1

1.11 g of aluminum sulfate, 8.1 g of water and 18.1 g of 40 wt. % TPAOH were mixed and stirred at 0° C. Then, 20.83 g of TEOS was added to the mixture and it was stirred at room temperature for 48 hours. The resulting slurry was dried in an oven at 110° C. for 10 hours. The dried products were placed in an autoclave at 170° C. for 5 days, in the presence of water. The resulting product is characterized in Table 1.

The autoclave treated product was mixed with appropriate amounts of large pore alumina and partially acid peptized alumina binder to form a mixture. The mixture was then extruded into 1.8 mm cylinders to form a shaped catalyst support. The shaped catalyst was dried overnight at 110° C. and then calcined at 500° C. for 4 hours. The calcined catalyst was impregnated with a $Ga(NO_3)_3$ solution, then dried at 110° C. for 10 hours, and calcined again at 550° C. for 4 hours.

It should be noted that the ZSM-5 of Comparative Example 1 has been calcined while the ZSM-5 of Inventive Example 1 has not.

TABLE 1

| ZSM-5 Nanoparticles | | |
|---|---|---|
| | Comparative Example 1 | Inventive Example 1 |
| Particle sizes (nm) | 196 | 30 |
| $SiO_2/Al_2O_3$ molar ratio | 40 | 37 |
| Product Yield (wt. %) | 65 | 80 |
| XRD phase | ZSM-5 | ZSM-5 |
| Crystallinity (CBV-5524 as reference) (%) | 77 | 98 |

TABLE 1-continued

ZSM-5 Nanoparticles

| | Comparative Example 1 | Inventive Example 1 |
|---|---|---|
| BET Surface Area (m$^2$/g) | 372 | 433 |
| pore volume (ml/g) | 0.32 | 0.39 |
| Microporous (ml/g) | 0.12 | 0.21 |
| Mesoporous (ml/g) | 0.2 | 0.18 |
| Average Pore Size (nm) | 34 | 46 |

Catalytic Testing

To understand the difference between the two catalysts, a pilot plant scale, hexane aromatization process was performed. The conditions were temperature=550° C., weight hour space velocity=12 h$^{-1}$, pressure=1 bar, n2/hexane volume ratio=1.2. The testing results are summarized in Table 2.

TABLE 2

Reaction performance comparison

| Catalyst | COMPARATIVE EXAMPLE 1 | INVENTIVE EXAMPLE 1 |
|---|---|---|
| Conversion (%) | 93.66 | 98.37 |
| H2 (wt. %) | 2.96 | 3.26 |
| Paraffin (wt. %) | 41.52 | 38.26 |
| Olefin (wt. %) | 10.27 | 6.70 |
| Naphthalene (wt. %) | 0.12 | 0.05 |
| Aromatics (wt. %) | 45.16 | 51.75 |

One distinction between Comparative Example 1 and Inventive Example 1 is that in Comparative Example 1, the ZSM-5 is calcined before mixing with the large pore alumina and binder. In contrast, the ZSM-5 of Inventive Example 1 is not calcined before introduction to the large pore alumina and binder.

As is shown in Table 2, when transitioning from the comparative example to the inventive example, overall conversion increased from 93.66 wt. % to 98.37 wt. %, the hydrogen yield increased from 2.96 wt. % to 3.26 wt. %. The yield of aromatics increased from 45.16 wt. % to 51.75 wt. %.

It is also noted that recitations herein of "at least one" component, element, etc., should not be used to create an inference that the alternative use of the articles "a" or "an" should be limited to a single component, element, etc.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A method of producing an aromatization catalyst, the method comprising:
   producing a plurality of uncalcined ZSM-5 nanoparticles via a dry-gel method, wherein the plurality of ZSM-5 nanoparticles has an average diameter of less than 80 nm;
   directly mixing the plurality of uncalcined ZSM-5 nanoparticles with large pore alumina and a binder to form a ZSM-5/alumina mixture; and
   calcining the ZSM-5/alumina mixture to form the aromatization catalyst; wherein the large pore alumina has a pore size of from 18 nm to 26 nm.

2. The method of producing an aromatization catalyst of claim 1, wherein the plurality of uncalcined ZSM-5 nanoparticles has not been subjected to centrifugation above 3,000 rpm, before being mixed with the large pore alumina and binder.

3. The method of producing an aromatization catalyst of claim 1, wherein the plurality of uncalcined ZSM-5 nanoparticles has not been subjected to calcination above 200° C. for more than 30 minutes, before being mixed with the large pore alumina and binder.

4. The method of producing an aromatization catalyst of claim 1, wherein the ZSM-5/alumina mixture is calcined at a temperature of from 400° C. to 700° C. for from 1 hour to 10 hours.

5. The method of producing an aromatization catalyst of claim 1, wherein the aromatization catalyst is impregnated with gallium atoms to form a Ga-ZSM-5 catalyst.

6. The method of producing an aromatization catalyst of claim 5, wherein the Ga-ZSM-5 catalyst is calcined.

7. The method of producing an aromatization catalyst of claim 1, wherein the aromatization catalyst is impregnated with a catalytic metal to form a metal-ZSM-5 catalyst, the metal-ZSM-5 catalyst comprises from 50 wt. % to 90 wt. % ZSM-5, 5 wt. % to 30 wt. % large pore alumina, 10 wt. % to 20 wt. % binder, and 0.2 wt. % to 6 wt. % catalytic metal.

8. The method of producing an aromatization catalyst of claim 7, wherein the catalytic metal comprises gallium.

9. The method of producing a catalyst of claim 1, wherein the directly mixing is extrusion.

10. The method of producing an aromatization catalyst of claim 1, wherein the plurality of uncalcined ZSM-5 nanoparticles has an average diameter 30 nm to 80 nm.

11. The method of producing an aromatization catalyst of claim 1, wherein at least 90% of the individual uncalcined ZSM-5 nanoparticles have diameters from 20 nm to 50 nm.

12. The method of producing an aromatization catalyst of claim 1, wherein an average pore size of the uncalcined ZSM-5 nanoparticles is from 35 nm to 55 nm.

13. The method of producing an aromatization catalyst of claim 1, wherein a BET surface area of the uncalcined ZSM-5 nanoparticles is from 300 m$^2$/g to 600 m$^2$/g.

14. The method of producing an aromatization catalyst of claim 1, wherein a pore volume of the uncalcined ZSM-5 nanoparticles is from 0.3 ml/g to 0.45 ml/g.

15. The method of producing a catalyst of claim 1, wherein the producing the plurality of uncalcined ZSM-5 nanoparticles via the dry-gel method comprises:
   combining an alumina source, a structure directing agent, and a silica source to form a slurry;

optionally, introducing NaOH to the slurry such that the final concentration of NaOH in the slurry is from 0.000001 g/L to 0.1 g/L;

drying the slurry to form a dry-gel; and autoclaving the dry-gel in a humidified autoclave to form the plurality of uncalcined ZSM-5 nanoparticles.

16. The method of producing an aromatization catalyst of claim 15, wherein the water content of the dry-gel is less than 25 wt. %.

17. The method of producing an aromatization catalyst of claim 15, wherein the dry-gel is not agitated during autoclaving.

\* \* \* \* \*